(12) United States Patent
Weller

(10) Patent No.: US 11,479,960 B1
(45) Date of Patent: Oct. 25, 2022

(54) ONCOLOGY VAULT STRUCTURE

(71) Applicant: Weller Construction, Inc., Columbia, CA (US)

(72) Inventor: Jeffrey James Weller, Columbia, CA (US)

(73) Assignee: Weller Construction, Inc., Columbia, CA (US)

( * ) Notice: Subject to any disclaimer, the term of this patent is extended or adjusted under 35 U.S.C. 154(b) by 262 days.

(21) Appl. No.: 16/895,137

(22) Filed: Jun. 8, 2020

Related U.S. Application Data

(60) Provisional application No. 62/859,931, filed on Jun. 11, 2019.

(51) Int. Cl.
| | |
|---|---|
| *E04B 1/04* | (2006.01) |
| *A61G 10/00* | (2006.01) |
| *E04B 1/92* | (2006.01) |
| *E04B 1/343* | (2006.01) |
| *E04B 2/08* | (2006.01) |
| *E04B 7/20* | (2006.01) |
| *E04H 3/08* | (2006.01) |
| *G21F 7/00* | (2006.01) |

(Continued)

(52) U.S. Cl.
CPC .............. *E04B 1/043* (2013.01); *A61G 10/00* (2013.01); *A61N 5/1077* (2013.01); *E04B 1/34321* (2013.01); *E04B 1/34384* (2013.01); *E04B 1/92* (2013.01); *E04B 2/08* (2013.01); *E04B 7/20* (2013.01); *E04H 3/08* (2013.01); *G21F 3/00* (2013.01); *G21F 7/00* (2013.01); *A61N 2005/1094* (2013.01); *E04B 2001/34389* (2013.01); *E04B 2001/925* (2013.01); *E04B 2002/0204* (2013.01)

(58) Field of Classification Search
CPC .. E04B 1/043; E04B 1/34321; E04B 1/34384; E04B 1/92; E04B 2/08; E04B 7/20; E04B 2001/34389; E04B 2001/925; E04B 2002/0204; A61G 10/00; E04H 3/08; G21F 3/04; G21F 7/00; A61N 2005/1094
See application file for complete search history.

(56) References Cited

U.S. PATENT DOCUMENTS

| | | | | |
|---|---|---|---|---|
| 1,758,903 | A | * | 5/1930 | Willets ...................... E04B 2/08 52/591.2 |
| 2,453,918 | A | * | 11/1948 | Jansen ................ E04B 1/34321 52/590.2 |

(Continued)

*Primary Examiner* — Rodney Mintz
(74) *Attorney, Agent, or Firm* — Heisler & Associates

(57) ABSTRACT

A plurality of wall cells rest upon an underlying cementitious foundation and form a perimeter of the vault. Each wall cell has two lateral sides with mating surfaces thereon which are of complementary undulating shape with adjacent lateral surfaces of adjacent wall cells. The wall cells have different thicknesses and widths to provide desirable wall thickness for a different portions of the oncology vault. A door assembly formed of specialized wall cells and with a pivoting door element are also included within the wall. A ceiling is provided above space inboard of the wall cells. This ceiling is formed of separate ceiling slab elements. The slabs are stacked in at least one layer. In one embodiment, multiple layers of slabs are stacked with seams between slabs of each layer offset from each other. In another embodiment, lateral sides of the slabs have a complementary undulating shape.

14 Claims, 5 Drawing Sheets

(51) Int. Cl.
    *G21F 3/00*     (2006.01)
    *A61N 5/10*     (2006.01)
    *E04B 2/02*     (2006.01)

(56) References Cited

U.S. PATENT DOCUMENTS

| | | | | |
|---|---|---|---|---|
| 2,720,105 A * | 10/1955 | Billups | G21F 3/04 | 376/288 |
| 2,942,115 A * | 6/1960 | O'Connell | G21F 3/04 | 250/517.1 |
| 2,970,218 A * | 1/1961 | Shaw | G21F 3/04 | 250/517.1 |
| 3,436,544 A * | 4/1969 | Graf, Jr. | G21C 11/02 | 250/517.1 |
| 3,614,446 A * | 10/1971 | Leuthold | G21F 3/04 | 250/517.1 |
| 3,732,831 A * | 5/1973 | Marciniak | E05G 1/024 | 109/82 |
| 3,995,165 A * | 11/1976 | Buth | G21F 3/04 | 976/DIG. 335 |
| 4,290,246 A * | 9/1981 | Hilsey | E04H 3/00 | D25/19 |
| 4,338,757 A * | 7/1982 | Witschi | E04G 21/125 | 52/378 |
| 4,698,943 A * | 10/1987 | Wieland | E04B 1/92 | 52/169.5 |
| 5,241,573 A * | 8/1993 | Thacker | G21F 3/04 | 250/517.1 |
| 5,504,344 A * | 4/1996 | Stein | G21F 3/00 | 250/496.1 |
| 5,536,111 A * | 7/1996 | Doernemann | E02B 3/06 | 405/21 |
| 5,633,508 A * | 5/1997 | Schleppenbach | G21F 3/04 | 250/517.1 |
| 5,695,443 A * | 12/1997 | Brent | G21F 3/04 | 405/129.55 |
| 5,852,643 A * | 12/1998 | Copson | G21F 5/005 | 250/517.1 |
| 6,058,672 A * | 5/2000 | McClellan | E04B 1/04 | 52/592.1 |
| 6,385,942 B1 * | 5/2002 | Grossman | E04C 2/049 | 52/630 |
| 6,418,686 B1 * | 7/2002 | Record | E04C 2/288 | 52/412 |
| 6,973,758 B2 * | 12/2005 | Zeik | E04H 1/125 | 52/561 |
| 7,134,805 B2 * | 11/2006 | Yee | F16L 13/113 | 52/592.1 |
| 7,291,854 B2 * | 11/2007 | Bichay | G21F 7/00 | 250/517.1 |
| 7,395,999 B2 * | 7/2008 | Walpole | E04D 3/351 | 52/564 |
| 7,665,249 B2 * | 2/2010 | Zeik | G21F 3/04 | 52/79.1 |
| 7,677,832 B2 * | 3/2010 | Yee | E04B 5/023 | 404/49 |
| 7,728,315 B2 * | 6/2010 | Bichay | G21F 7/00 | 250/517.1 |
| 7,820,993 B2 * | 10/2010 | Fehrenbacher | G21F 3/00 | 250/517.1 |
| 8,101,932 B2 * | 1/2012 | Bichay | G21F 7/00 | 250/517.1 |
| 8,459,714 B2 * | 6/2013 | Pomper | A61N 5/1001 | 250/493.1 |
| 8,742,382 B2 * | 6/2014 | Hindley | G21C 11/06 | 250/517.1 |
| 8,950,149 B2 * | 2/2015 | Stahl | E04H 7/18 | 52/592.2 |
| 9,027,297 B2 * | 5/2015 | Lefkus, III | E04B 1/34321 | 52/234 |
| 9,171,649 B2 * | 10/2015 | Zeik | E04H 1/1205 | |
| 9,388,442 B2 * | 7/2016 | Medoff | H01J 37/317 | |
| 9,777,430 B2 * | 10/2017 | Medoff | D21C 9/007 | |
| 10,265,232 B2 * | 4/2019 | Yim | E04B 1/92 | |
| 10,350,548 B2 * | 7/2019 | Medoff | C12P 7/06 | |
| 2002/0166293 A1 * | 11/2002 | Zeik | E04H 1/125 | 52/79.1 |
| 2005/0220539 A1 * | 10/2005 | Yee | E04B 5/04 | 404/40 |
| 2005/0247013 A1 * | 11/2005 | Walpole | E04B 7/22 | 52/741.1 |
| 2006/0096199 A1 * | 5/2006 | Zeik | E04B 1/92 | 52/250 |
| 2006/0179757 A1 * | 8/2006 | Schulner | E04B 7/20 | 52/459 |
| 2007/0012888 A1 * | 1/2007 | Bichay | G21F 7/00 | 250/496.1 |
| 2007/0081858 A1 * | 4/2007 | Yee | E04B 5/04 | 404/40 |
| 2008/0023658 A1 * | 1/2008 | Bichay | G21F 7/00 | 250/517.1 |
| 2008/0203331 A1 * | 8/2008 | Murphy | A61N 5/10 | 250/517.1 |
| 2008/0308754 A1 * | 12/2008 | Fehrenbacher | G21F 7/00 | 250/517.1 |
| 2010/0146870 A1 * | 6/2010 | Zeik | E04B 1/3483 | 52/741.3 |
| 2010/0193713 A1 * | 8/2010 | Bichay | G21F 7/00 | 250/517.1 |
| 2012/0017520 A1 * | 1/2012 | Hur | E04H 9/021 | 52/79.11 |
| 2012/0112092 A1 * | 5/2012 | Pomper | A61N 5/1001 | 250/492.1 |
| 2013/0111825 A1 * | 5/2013 | Lefkus, III | E04B 1/34321 | 52/173.1 |
| 2013/0270460 A1 * | 10/2013 | Erasmus | G21C 11/06 | 250/505.1 |
| 2013/0312358 A1 * | 11/2013 | Stahl | E04C 2/04 | 52/604 |
| 2014/0284494 A1 * | 9/2014 | Medoff | H01J 37/317 | 198/339.1 |
| 2015/0240473 A1 * | 8/2015 | Lefkus, III | E04B 1/34384 | 52/79.1 |
| 2016/0038766 A1 * | 2/2016 | Zeik | A61N 5/10 | 600/1 |
| 2017/0036185 A1 * | 2/2017 | Medoff | C12M 47/10 | |
| 2018/0016745 A1 * | 1/2018 | Medoff | C12P 19/14 | |
| 2018/0110666 A1 * | 4/2018 | Yim | E04H 3/08 | |
| 2018/0258659 A1 * | 9/2018 | LeBlanc | E04B 7/20 | |
| 2019/0029147 A1 * | 1/2019 | Cordes | B32B 15/088 | |
| 2019/0316294 A1 * | 10/2019 | Medoff | C10G 1/02 | |
| 2020/0037475 A1 * | 1/2020 | Rausch | E04B 1/92 | |
| 2020/0362556 A1 * | 11/2020 | Lem | E04B 1/92 | |
| 2022/0034084 A1 * | 2/2022 | Lefkus | E04B 1/92 | |
| 2022/0170264 A1 * | 6/2022 | Badin Cherit | E04B 5/263 | |

* cited by examiner

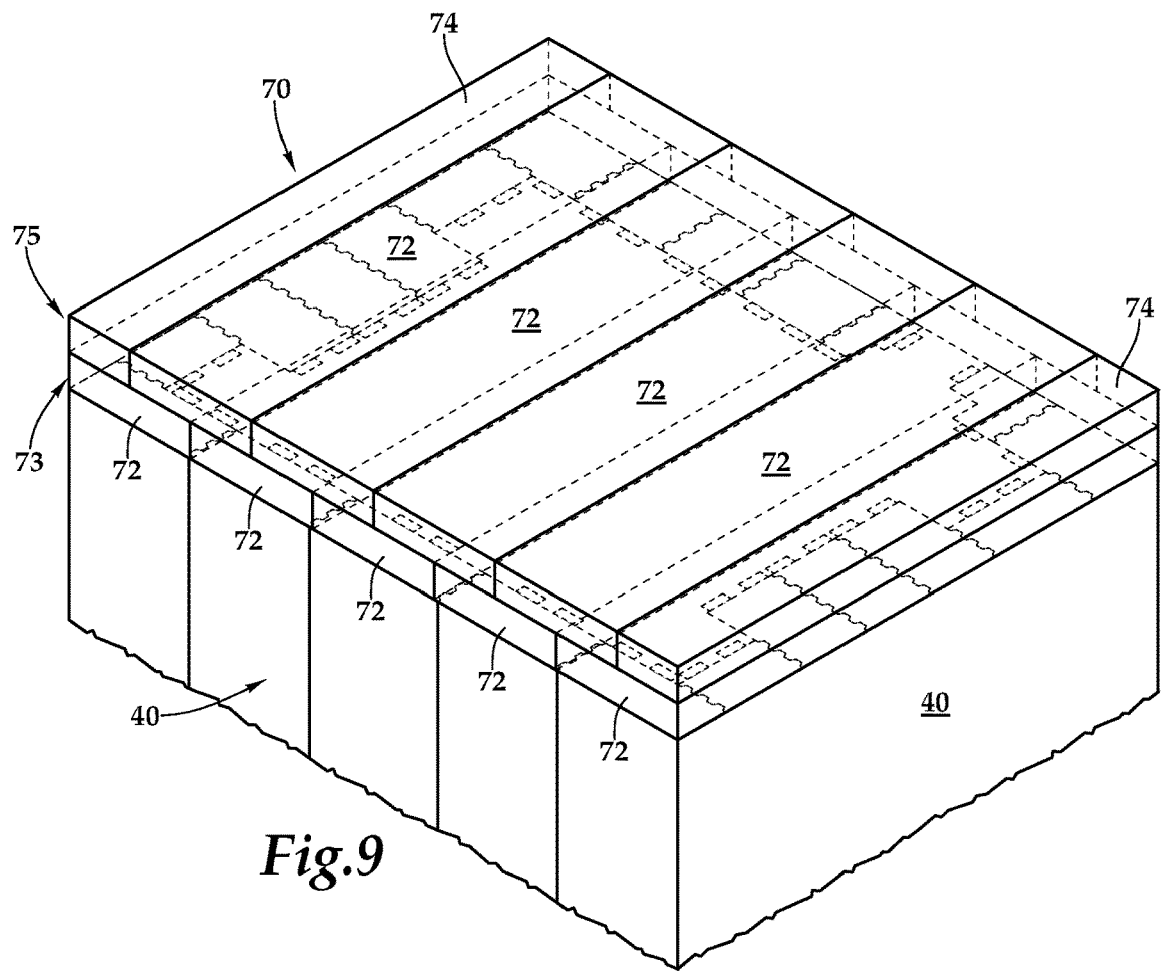
Fig.9
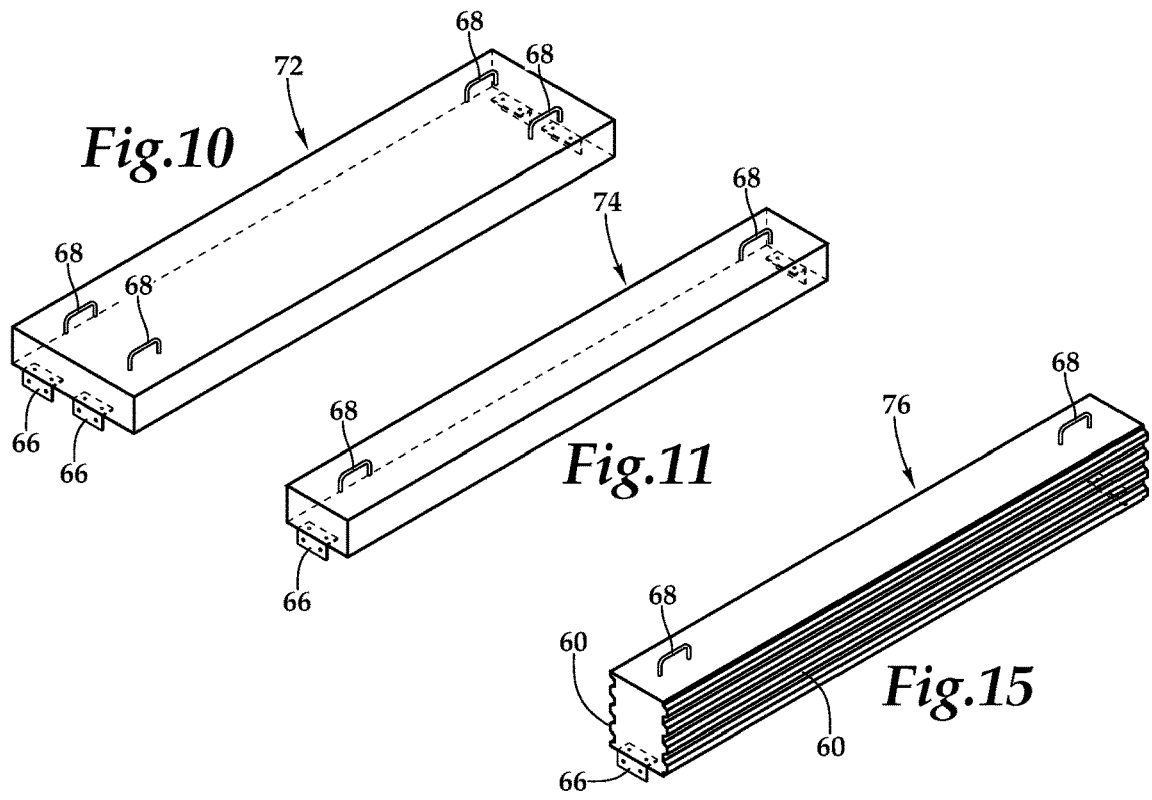
Fig.10
Fig.11
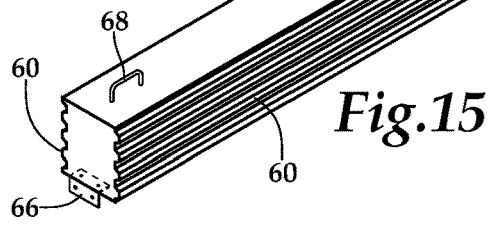
Fig.15

ONCOLOGY VAULT STRUCTURE

CROSS-REFERENCE TO RELATED APPLICATIONS

This application claims benefit under Title 35, United States Code § 119(e) of U.S. Provisional Application No. 62/859,931 filed on Jun. 11, 2019.

FIELD OF THE INVENTION

The following invention relates to permanent and temporary buildings configured for containment of radiation, such as an oncology vault. More particularly, this invention relates to modular buildings made up of separate cells and slabs and configured to prevent radiation sources within an interior thereof from substantially escaping the structure.

BACKGROUND OF THE INVENTION

Efficient and effective delivery of oncology medical services involves management of unique challenges, among which are challenges associated with exposure to doses of radiation which can be detrimental to oncology medical personnel, and potentially also patients if not delivered according to appropriate protocols. To minimize exposure to radiation during oncology treatments which involve nuclear radiation, such treatments are often delivered in a treatment room which has appropriate shielding to prevent radiation (e.g. subatomic particle radiation including protons, neutrons, electrons and high energy photonic radiation) from escaping from the radiation dose delivery site. Furthermore, minimization of radiation exposure is a priority in locations where radiation sources are located, either for storage of radiation sources and/or for containment of nuclear particle generation equipment, such as various different forms of particle accelerators.

Often oncology dose delivery sites are incorporated into (or near) a medical office building where other related medical services are provided. In such a location, careful consideration must be given as to how to properly contain sources of radiation, while still providing convenient access to the radiation dose delivery location for patients and authorized personnel.

In other instances, a critical need exists for an oncology radiation dose delivery facility when insufficient time is available to construct a permanent facility. Hence, it is desirable to be able to at least provide a temporary radiation containment structure so that needs for radiation dose delivery can be provided within a temporary facility where permanent facilities do not exist or have exceeded their capacity, and before permanent facilities can be constructed. Such temporary facilities could be configured both for rapid construction on site, and also potentially for disassembly when no longer needed, and potentially transport and reassembly at other locations if desired.

While the challenges in design and construction of containment facilities for oncology radiation dose delivery and storage facilities are certainly known, significant complexity and associated expenses are involved with design and construction of such facilities. Specialty designers are often involved. Shielding materials can be exceptionally heavy and large, thus requiring extensive involvement of specialized structural engineers, architects and other professionals in the design of such facilities. Furthermore, during construction unique expertise is involved in the on-site construction of containment facilities and effectively managing construction processes including interfacing with local building departments on such unique and complex structures, as well as other regulatory bodies with jurisdiction when nuclear radiation is involved.

With such challenges and complexity, significant expense can be associated. Such expense must then be factored into the amounts charged for patients to receive oncology treatments, and for oncologists to rent or otherwise enjoy authorized use of such oncology facilities. As healthcare costs increase, the burden on society generally, and particularly on those paying for the healthcare services, can become a significant burden. If oncology radiation source containment structures can be designed and manufactured to have a modular form for at least some components thereof, and to be designed in a manner which has a basic form which can be suitable for a variety of different locations, and which can be designed with simplicity of manufacture in mind from the beginning, an opportunity exists to provide oncology containment structures which can be significantly less expensive to design and to construct, providing benefits both to medical facilities, medical professionals, and their patients. Furthermore, oncology radiation dose delivery containment structures having a standardized form and with portions thereof which can potentially be pre-fabricated, present the opportunity for significant reduction in the timeline required for manufacture and installation/construction. Such time savings can also translate into cost savings and also allow for the benefits of the oncology treatments to be provided in the facility to be made available more quickly.

While the needs identified above are described in the context of oncology radiation dose delivery facilities and associated facilities for storage and/or generation of suitable radiation oncology treatments, a corresponding need exists for other nuclear radiation handling facilities, such as laboratories, and educational facilities. Thus, while the invention described herein is primarily directed toward oncology radiation dose delivery facilities, this invention can be suitably adapted (with little or no modification) to other such radiation handling facilities.

SUMMARY OF THE INVENTION

With this invention, an oncology vault structure is provided which is particularly suited for either temporary or permanent construction and for either pre-fabrication of elements thereof offsite before assembly at a final location, or construction onsite at a final facility. The vault has a design which is provided to have suitable radiation absorption characteristics and radiation containment characteristics, so that only authorized personnel and authorized patients are exposed to measurable doses of radiation. Such authorized personnel can monitor radiation dosage, such as with dosimetry badges, so that total radiation exposure limits are not exceeded, while beneficial radiation doses can be provided to patients for therapeutic benefit.

The vault includes three basic parts: a foundation/footing at a lower portion thereof, wall cells which together form walls of the vault and slabs defining a roof of the vault. Access into the vault typically is provided through a pivoting door which is formed in a portion of the wall. One example floor plan configuration for the walls is depicted in included figures, along with other details for the foundation/footing, ceiling slabs and other details according to one embodiment of this invention.

While the foundation/footing could conceivably be formed of movable slabs similar to the ceiling, in this example the footing is a monolithic structure typically formed of concrete poured onsite with appropriate reinforcing steel embedded therein. The footing typically has a smooth horizontal upper surface, except for an optional equipment pit centered within a floor of the vault.

The walls, are formed of individual cells which fit together to form the walls of the vault. Many of the cells have a similar size and shape, but many of the cells also have a distinct size and shape, configured to fit together to form the walls of the overall vault. Particular specifications of various different wall cells are shown in the included drawings. Each wall cell includes an inwardly facing surface and an outwardly facing surface, which are typically generally parallel to each other and spaced apart by a thickness of the wall cells. In one particular embodiment, the wall cells either have a standard thickness or an increased thickness which is approximately double the standard thickness. Increased thickness wall cells can be provided at areas where radiation is expected to be concentrated. In this particular embodiment, such concentration is at ends of the vault centered on and the walls which are most distant from each other.

The inwardly facing surface and outwardly facing surface are preferably both substantially smooth and oriented in vertical planes. Each wall cell also includes a top surface and a bottom surface defining a height of each wall cell. The bottom surface is configured to be placed adjacent to the foundation/footing. The top surface is configured to be placed beneath the ceiling. These top and bottom surfaces of each wall cell are preferably planar and parallel with each other, and perpendicular to the inwardly facing surface and the outwardly facing surface.

Each wall cell also includes lateral sides which are configured to abut adjacent wall cells. These lateral sides preferably have an undulating contour which matches the contour of adjacent cells. In one embodiment, light gauge steel deck material is provided at these lateral sides of each wall cell. These light gauge steel deck elements are typically attached to the wall cells by having the concrete or other cementitious material poured into a form between the steel deck elements, in a manner allowing the steel deck elements to be bonded to the concrete or other cementitious material within a core of each wall cell. As an alternative, the steel deck material (or other forms) could be removed after hardening of the concrete, so that the lateral sides have a shape matching that of the forms which have been removed.

Whether the light gauge steel deck elements remain or are removed, the lateral sides of each wall cell have a complementary non-planar undulating form when placed adjacent to another wall cell having a similar and complementary form on the lateral side. The undulating form of these lateral sides of each wall cell prevents a straight line path from existing between adjacent wall cells, which straight line path might be traveled by nuclear radiation and escape the vault. Instead, such radiation passes through significant amounts of concrete, designed to absorb a sufficiently large amount of the radiation that no hazardous dose of radiation extends beyond the wall cells. Furthermore, the undulating form of these lateral sides helps the wall cells to support each other from a structural standpoint.

Typically, the wall cells include grabbable hook bars extending from upper portions of each wall cell, either within recessed portions of top surfaces of each wall cell, or extending up from such top surfaces of such wall cells, and typically fitting within appropriately located recesses in slab elements forming the ceiling of the vault. Such hook bars allow for a crane or other overhanging construction equipment element to grab, lift and place the wall cells, both for construction and potentially also for disassembly of the vault.

Various angle brackets are preferably provided at upper and lower corners with the lower corners defining a junction between the foundation/footing and the bottom surface of each wall cell. These angle brackets can be formed of steel or other high strength material. Upper corner angle brackets are interposed between the top surface of each wall cell on the inwardly facing portion of each wall cell, and portions of the slabs forming the ceiling of the vault. In one embodiment, these angle brackets are put into place after placement of the wall cells upon the foundation and after placement of ceiling slab elements upon the wall cells. For instance, holes can be drilled in the cementitious material forming the footing, wall cells, and ceiling slabs at appropriate locations matching holes in the angle brackets. Angle brackets are then appropriately placed and fasteners (and/or adhesives) are utilized to secure the angle brackets between the foundation and wall cells, and between the wall cells at the ceiling.

These base and ceiling angle brackets thus act as fasteners to secure the wall cells to the foundation and the ceiling slab elements to the wall cells. As an alternative, these angle brackets could be permanently affixed to one element and removable affixed to another element, to allow for the angle brackets to remain with either the footing, wall cells or ceiling slab elements, when disassembly is desired. While the angle brackets are shown within an interior of the vault, these angle brackets could conceivably be provided on an exterior of the vault as an alternative, especially if the foundation/footing and/or ceiling slab elements are large enough to extend beyond the outwardly facing surfaces of the wall cells.

The ceiling is typically formed from a series of ceiling slab elements provided in two different layers including a lower layer of slabs and an upper layer of slabs (with an optional single layer embodiment also disclosed). Each slab is preferably generally rectangular in cross-section. The lower layer of slabs in this embodiment is shown with five such slabs spanning a shorter dimension of the floor plan of the vault. These five slabs have a similar width and completely cover the interior space inboard of the wall cells. The second and upper layer of the ceiling is provided by six upper slabs. Four of these upper slabs are similar in size to the five lower slabs. Two half width slabs are provided in the upper layer of ceiling slabs at extreme edges thereof. The upper slabs are provided extending similar to the lower slabs spanning a shorter plan width of the vault. In this way, seams between the lower slabs are covered by the upper slabs. Furthermore, seams between the upper slabs are covered by the lower slabs. Any radiation directed upwardly toward the ceiling is thus not able to find a gap between both lower slabs and upper slabs. Rather, any radiation aligned with gaps between lower slabs would impact the upper slabs, and radiation containment is correspondingly maintained at appropriately safe levels.

In the single layer embodiment, each slab has edges of complementary serpentine (undulating or crenelated) form. Such form can generally match the seams between adjacent wall cells. With such a form, radiation is not able to find a path out of the ceiling of the vault without encountering the thick slabs on one side or the other (or both) of such a seam between ceiling slabs.

Other details of the vault of this invention can be further provided in various different embodiments of this invention. Dimensions of the vault can be altered, including size of a floor plan, wall thicknesses, ceiling thicknesses, footing/ foundation thicknesses and shape of the vault. Some of the wall cells are modified because they are located at corners of the vault, so that laterals sides of the wall cells with undulating contours are provided on adjacent vertical surfaces of the wall cells, rather than on opposite vertical surfaces of the wall cells.

The vault can be provided as a standalone structure or can be incorporated into other construction built around or directly adjacent to exterior portions of the vault. Within an interior of the vault, in one embodiment, interior studs are framed therein and wall surfacing materials are provided, to facilitate hanging of cupboards and other equipment upon walls of the vault and for acoustic and other purposes. Flooring material can be provided upon the footing. Ceiling treatment can also be provided within the vault, such as a "dropped ceiling" suspended from the lower layer of ceiling slabs, and providing utility space above ceiling tiles through which electrical wiring and heating ventilating and air conditioning (HVAC) equipment can be routed. Routing of electrical service and HVAC service conduits can occur at a predefined location, such as above a door into the vault, with appropriate consideration provided to avoid such access being a potential point of radiation escape in undesirable amounts from the vault. For instance, additional radiation shielding can be provided adjacent such access points, or access pathways can be provided with sufficient bends therein or other contours, to prevent radiation passage therethrough. As another alternative, self-contained power and/or ventilation systems can be utilized.

OBJECTS OF THE INVENTION

Accordingly, a primary object of the present invention is to provide an oncology vault of modular construction which is configured to contain radiation therein.

Another object of the present invention is to provide an oncology vault which is structurally sound.

Another object of the present invention is to provide an oncology vault or other radiation containing structure which is configured in a manner which lends itself to ease of construction and de-construction.

Another object of the present invention is to provide an oncology vault which is of a modular form with individual modules thereof positionable with a crane, and sized and weighted in a manner which enables offsite manufacture and simple transport for installation at the location of the oncology vault or other radiation containing structure.

Another object of the present invention is to provide an oncology vault which can be a temporary structure formed of modular elements which can be brought together during construction, and then separated from each other later should deconstruction be desired.

Another object of the present invention is to provide a method for constructing an oncology vault or other radiation containing structure which effectively contains radiation therein and which is structurally sound and straightforward to construct and deconstruct.

Another object of the present invention is to provide a modular structure formed of separate wall cells and ceiling slab elements which are configured to contain radiation from escaping from within, and which can be readily constructed and deconstructed from separate wall and ceiling modules.

Other further objects of the present invention will become apparent from a careful reading of the included drawing figures, the claims and detailed description of the invention.

BRIEF DESCRIPTION OF THE DRAWINGS

FIG. 9 is a perspective view of an upper portion of the oncology vault with the ceiling formed of multiple layers of ceiling slabs, and with portions of the walls hidden by the ceiling slab shown in broken lines.

FIG. 10 is a perspective view of a full size ceiling slab according to one embodiment of this invention.

FIG. 11 is a perspective view of a half-size ceiling slab according to one embodiment of this invention.

FIG. 15 is a perspective view of an interlocking ceiling slab element of the alternate ceiling embodiment of FIG. 14.

DESCRIPTION OF THE PREFERRED EMBODIMENT

Figure 1:
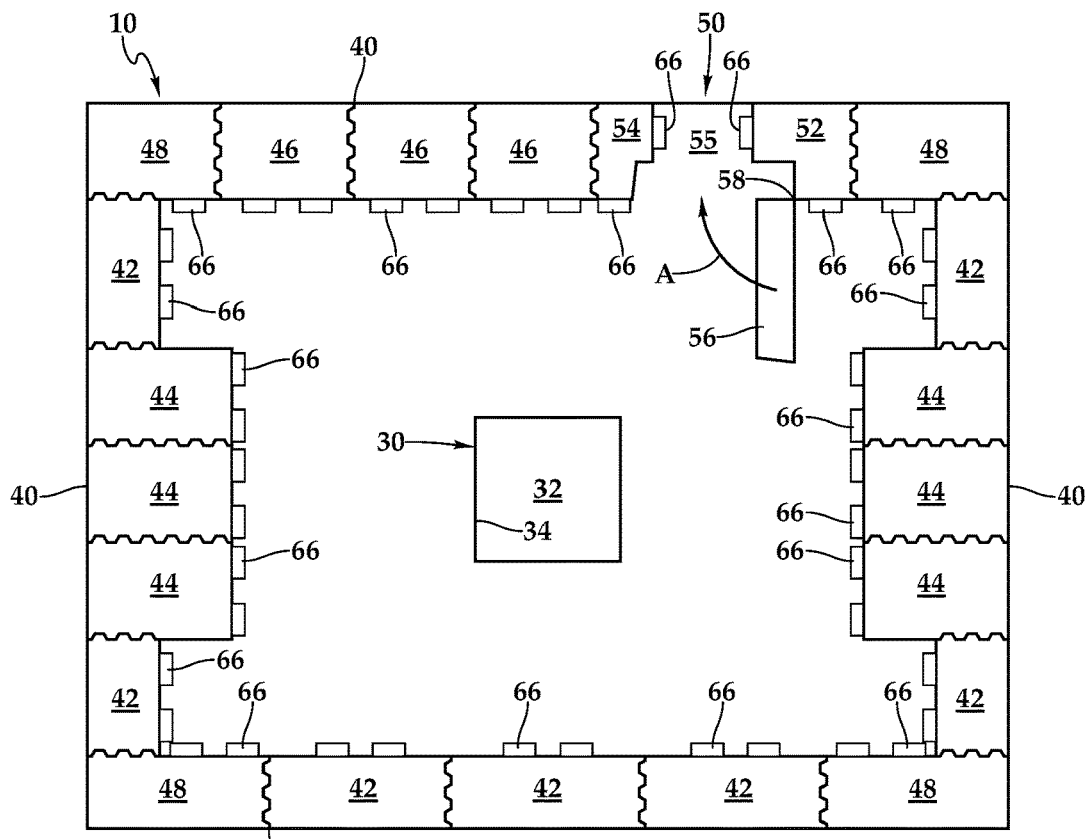
FIG. 1 is a top plan view of the oncology vault of one embodiment of this invention with the ceiling removed and showing how individual wall cells fit together around the perimeter of the oncology vault according to one embodiment.
Figures 2, 3:
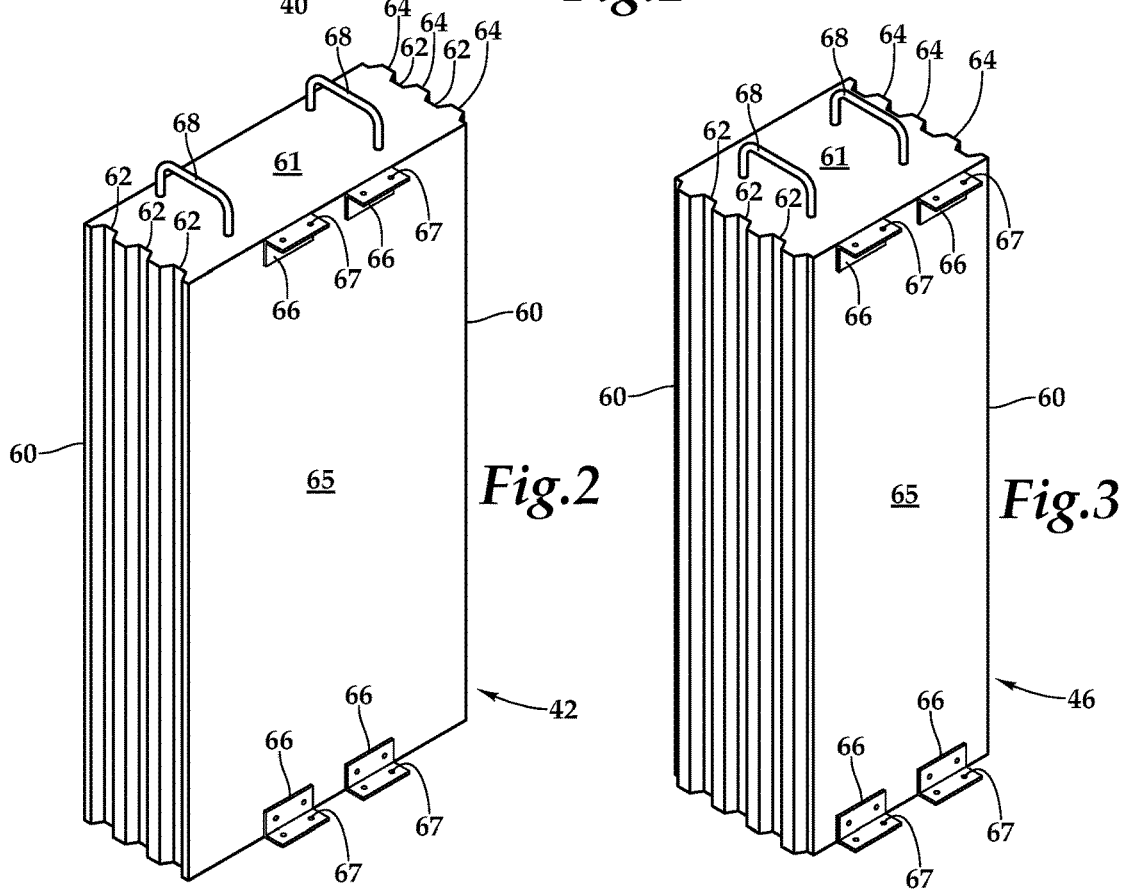
FIG. 2 is a perspective view of a wide cell forming a portion of the wall of the structure of this invention according to FIG. 1.
FIG. 3 as a perspective view of a square cell forming a portion of the wall of the structure of this invention according to FIG. 1.
Figure 4:
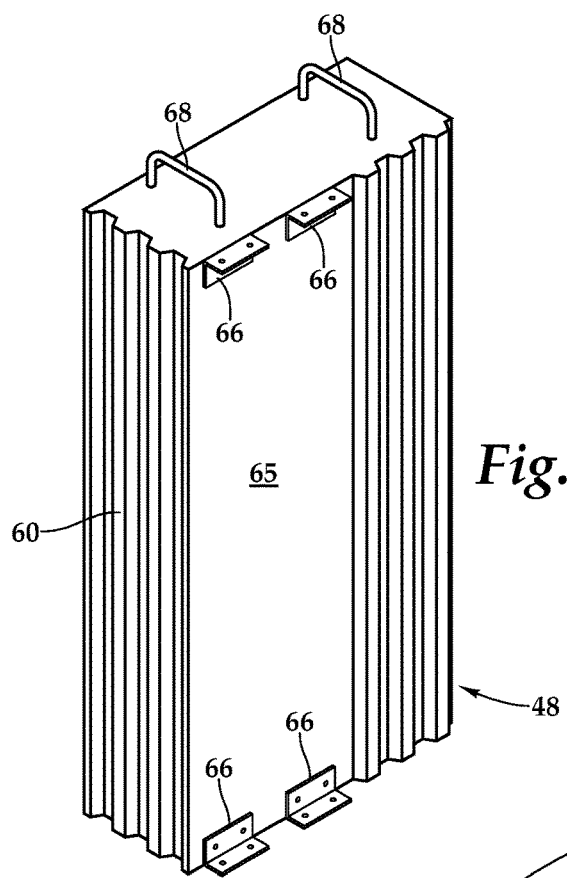
FIG. 4 is a perspective view of a corner cell forming a portion of the wall of the structure of this invention according to FIG. 1.
Figure 5:
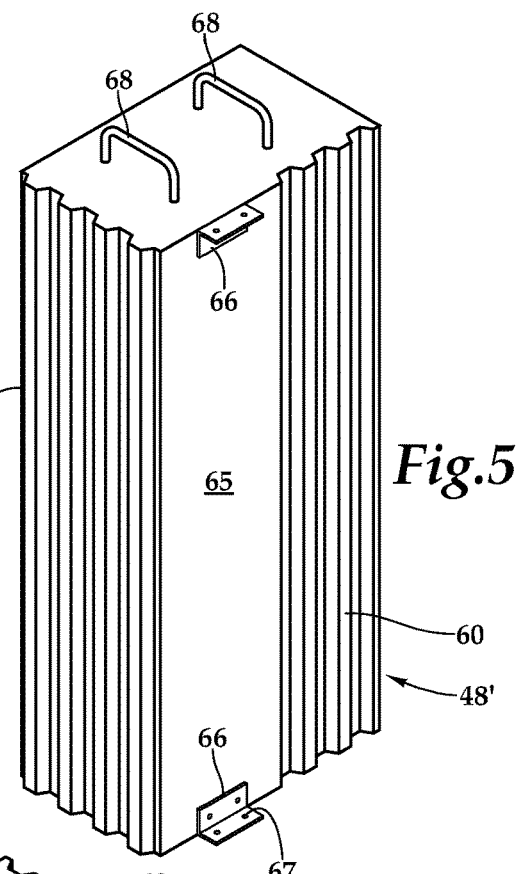
FIG. 5 is a perspective view of an alternative corner cell forming a portion of the wall of the structure of this invention according to FIG. 1.
Figure 6:
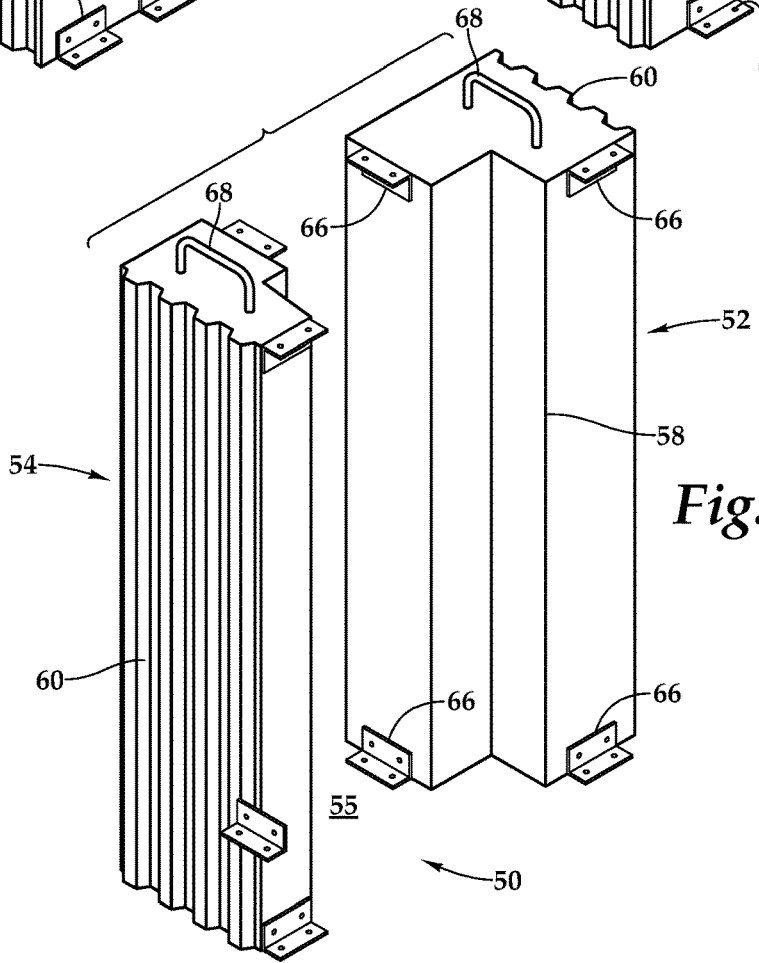
FIG. 6 is a perspective view of a door assembly for use within a portion of a wall of the structure of this invention according to FIG. 1.
Figure 7:
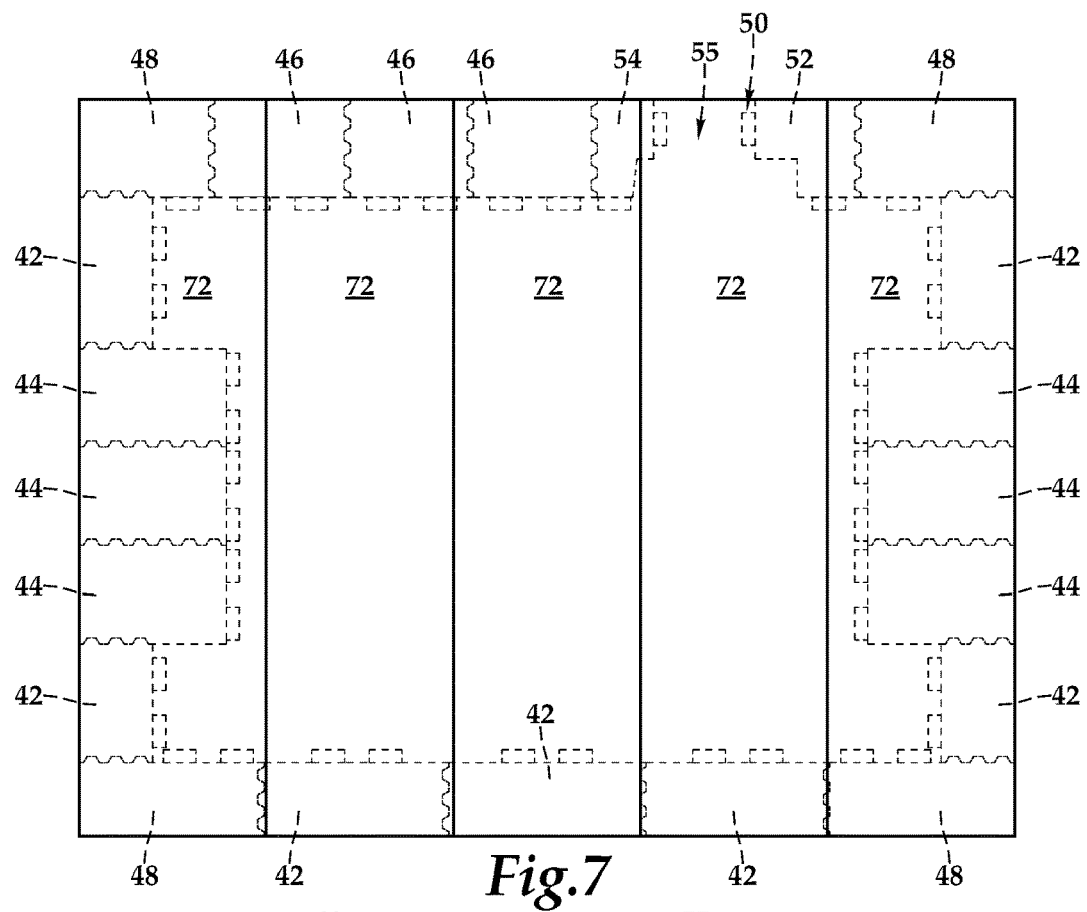
FIG. 7 is a top plan view of the oncology vault of this invention with the walls shown in broken lines beneath a first layer of ceiling slab elements forming at least a portion of a ceiling of the oncology vault of this invention.
Figure 8:
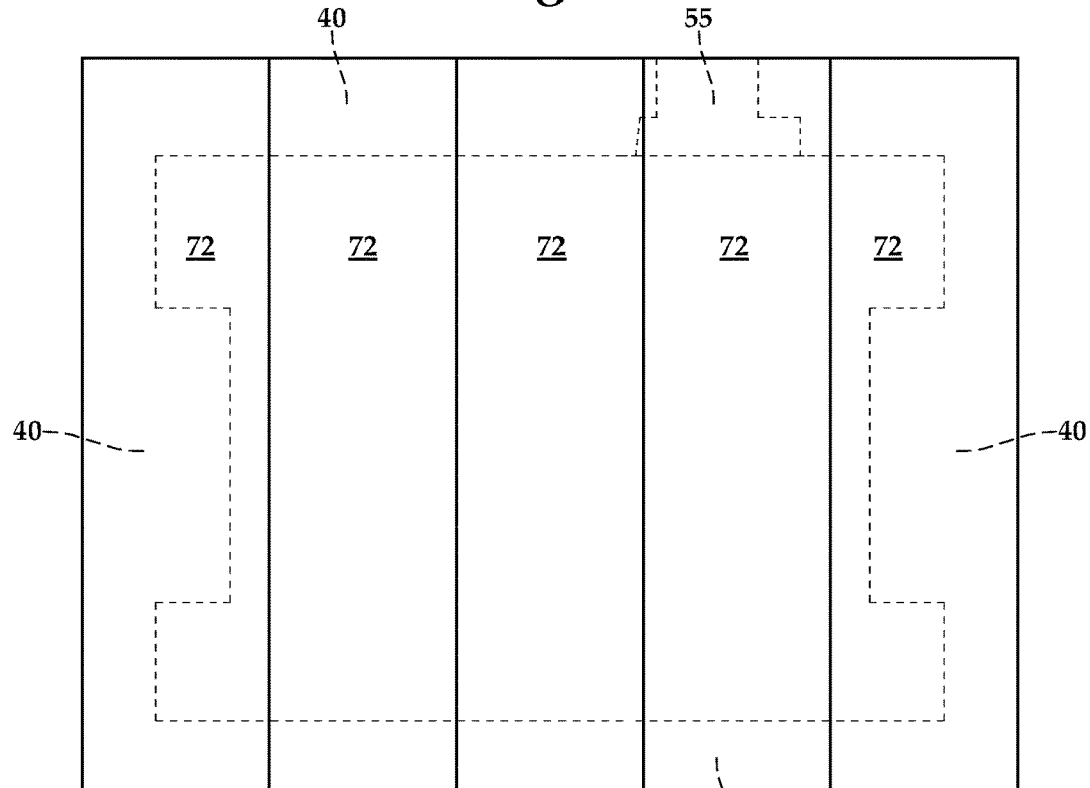
FIG. 8 is a top plan view of the oncology vault of one embodiment of this invention with the foundation at a lowermost portion of the vault shown in broken lines.

Referring to the drawings, wherein like reference numerals represent like parts throughout the various drawing figures, reference numeral 10 is directed to an oncology vault defining a space where a radiation producing machine or other radiation source can be placed, with radiation emanating from such a source being substantially contained within the vault 10. The vault 10 is configured of modular elements which act together to form the oncology vault 10, to simplify manufacture and also to allow for assembly and disassembly should the vault 10 be desired to be temporary in nature.

In essence, and with particular reference initially to FIGS. 1 and 9, basic details of the oncology vault 10 of this invention are described, according to one disclosed example. The vault 10 rests upon an underlying foundation 20 (see also FIGS. 12-14) typically formed of cementitious material. A pit 30 can be provided in this foundation 20, such as a central location, such as to facilitate mounting of machinery from which radiation emanates, such as when providing oncology treatments. A plurality of wall cells are placed upon this foundation around the perimeter of an interior space of the vault 10. The plurality of wall cells 42, 44, 46, 48 can have different configurations to provide particular wall thicknesses and overall geometry desired for the vault 10. The wall cells have lateral sides defining mating surfaces of complementary shape which are placed adjacent to each other. In this embodiment, this complementary shape is in the form of undulating surfaces 60 which both structurally provide support between the individual wall cells 42, 44, 46, 48 and also prevent seams between the wall cells 42, 44, 46, 48 providing any linear pathway along which radiation could pass and escape the vault 10. A door assembly 50 is also provided within a portion of one of the walls 40 of the vault 10.

A ceiling 70 is provided in the form of a series of ceiling slab elements 72, 74 having ends thereof resting upon the walls 40. In one embodiment, full size slabs 72 are provided in a lower layer 73. An upper layer 75 rests upon the lower layer 73 which includes full slabs 74 positioned with seams therebetween offset with seams in the lower layer 73, and with half slabs 74 at the end of the upper layer 75. With such offsetting of the seams, radiation escape along linear pathways is avoided. An alternate ceiling 80 includes interlocking slabs 76 including undulating surfaces 60 on lateral sides thereof to provide structural support therebetween and to eliminate linear paths through the alternate ceiling 80 and out of the vault 10.

More specifically, and with particular reference to FIGS. 1 and 12-14, details of the foundation 20 are described, according to this particular embodiment disclosed herein. The foundation 20 provides an underlying surface for the vault 10. This foundation 20 can differ based on underlying structures upon which the vault 10 is placed. Typically the vault 10 is placed upon underlying soil. Soil conditions can to some extent determine the type of foundation 20 required. Typically, the foundation 20 is a poured slab of cementitious material, but could be formed in other manners (e.g. prefabricated) of cementitious materials or other materials. A surface 22 defines an upper portion of the foundation 20. A perimeter of the surface 22 generally supports the walls 40 of the vault 10. If needed to provide adequate support, footings 24 (FIGS. 12-14) can be provided under portions of the foundation 20, such as where the walls 40 are to be placed.

Figure 13:
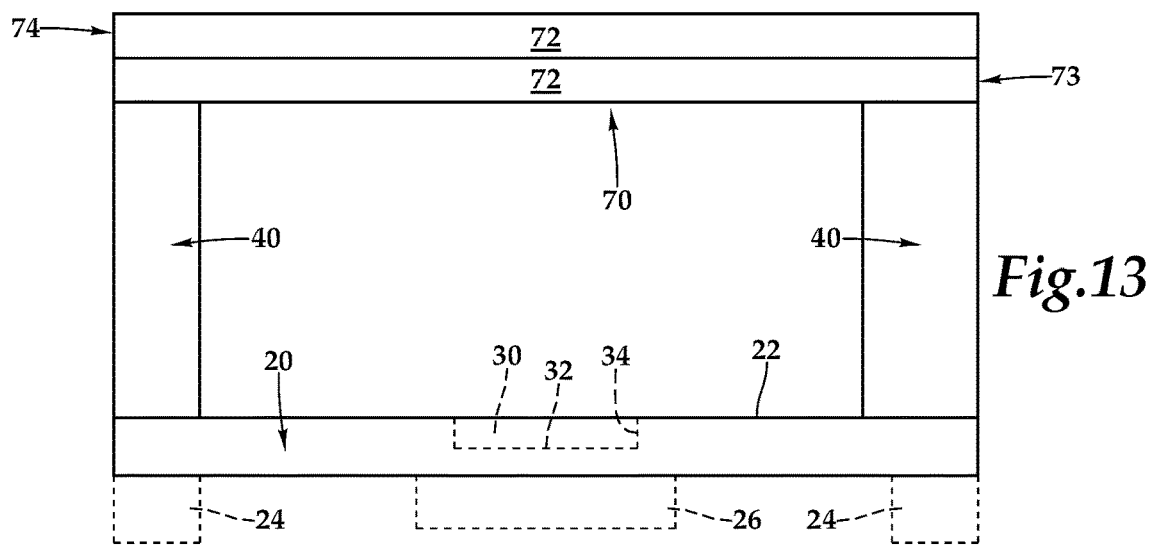
FIG. 13 is a side elevation full sectional view of that which is shown in FIG. 12 and showing the foundation, walls and ceiling of FIG. 12, along with optional pit for equipment support and optional footing elements shown in broken lines.
Figure 14:
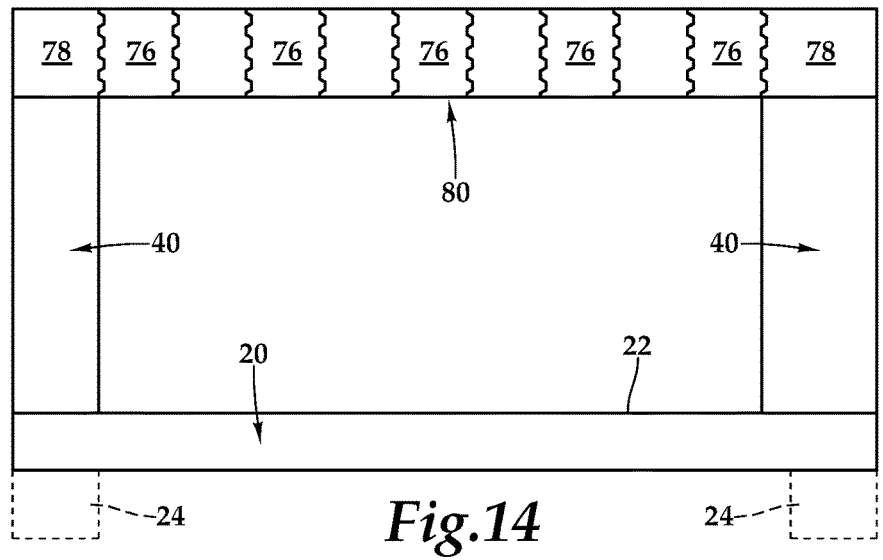
FIG. 14 is a side elevation full sectional view similar to that which is shown in FIG. 13, but with an alternative ceiling formed of interlocking slabs having undulating lateral surfaces for interlocking together, each of these interlocking slabs spanning a long dimension of the oncology vault in this particular embodiment, and with optional footings beneath the foundation shown in broken lines.

In one embodiment, the foundation 20 includes a pit 30 therein, which extends down from the surface 22. This pit 30 can provide a location for mounting of machinery to be used within the oncology vault 10. Such a pit 30 would generally include a floor 32 parallel with and below the surface 22 of the foundation. Perimeter sides 34 define a perimeter of the pit 30 and extend between the floor 32 and the surface 22 of other portions of the foundation 20. If needed, a central footing 24 of the foundation 20 can be of increased depth to support weight of machinery to be placed within the pit 30 (FIG. 13).

With particular reference to FIGS. 1-5, details of the walls 40 and various wall cells 42, 44, 46, 48 are described, according to this particular example. The walls 40 are formed of a plurality of separate cells 42, 44, 46, 48, so that the walls 40 have a modular construction. Such modularity assists in construction, in that lesser weight is involved for movement of each of the individual cells. As the walls 40 are substantially thick to contain radiation within the vault 10, weight of these cells 42, 44, 46, 48 can be significant. Hooks 68 are provided on the wall cells 42, 44, 46, 48. A door assembly 50 is also included within one of the walls 40 to provide access into and out of the vault 10 interior.

Wide cells 42 (FIG. 2) provide a portion of the walls 40. The wide cells are characterized by having inner and outer surfaces which are closer together then lateral surfaces which are located next to adjacent cells 42, 44, 46, 48 within the walls 40. Such wide wall cells 42 are generally approximately twice as wide as they are deep between inner and outer surfaces thereof, but can have a lesser width them this or a greater width than this, such as to provide a desired overall geometry and floor plan for the vault 10. Generally, the wide cells 42 are placed in locations where a lesser amount of radiation is anticipated. Generally, corners of the vault, being further from a central area where radiation generating machinery is located, and having a greater amount of overlapping material near corners of the vault 10, need lesser radiation shielding so that the wide cells 42 are appropriate.

Deep cells 44 (FIG. 1) also provide a portion of the walls 40. The deep cells are characterized in that they have a greater depth between inner and outer surfaces than a width between lateral surfaces which are located next to adjacent cells 42, 44, 46, 48. The deep wall cells 44 are placed in locations where greater amounts of radiation are anticipated, such as at ends of the vault 10 where beams of radiation might tend to impact the walls 40, so that a greater amount of radiation shielding is beneficially provided. The deep wall cells 44 are characterized in and they are approximately twice as deep as they are wide in a typical form. However, the deep wall cells 44 could be somewhat less than twice as deep as they are wide or somewhat greater than twice as deep as they are wide, and still generally be in the category of deep cells 44.

Square cells 46 (FIG. 3) also provide a portion of the walls 40. The square cells are characterized in that they have a similar depth between inner and outer surfaces as a width between lateral surfaces which are located next to adjacent cells 42, 44, 46, 48. Square cells 46 can be utilized when an intermediate amount of radiation shielding is considered to be desirable. The square cells 46 could have a slightly greater than equal or slightly less than equal ratio of width to depth and still be generally considered to be square cells 46.

Corner cells 48 (FIGS. 4 and 5) provide corners between the walls 40. The corner cells are characterized in that they have an outer corner and have lateral sides which are located next to adjacent cells 42, 44, 46, 48, which lateral sides are not opposite each other, but rather are generally next to each other, with perhaps some plain wall surface therebetween. The corner cells 48 are particularly configured to unite the separate walls 40 of the vault 10 together in a secure fashion for structural integrity and also in a manner which minimizes or eliminates any possibility of radiation escape from the vault 10. Some of the corner cells 48 are thicker (FIG. 4), while other of the corner cells 48' (FIG. 5) are thinner.

Such variation allows for matching configuration of cells 42, 44, 46 which are adjacent to lateral surfaces of the corner cells 48, 48'.

With particular reference to FIGS. 1 and 6-8 details of the doorway assembly are described, according to this particular disclosed embodiment. The doorway assembly includes specialized wall cells including a hinge cell 52 and a latch cell 54. These cells 52, 54 within the door assembly 50 are located on either side of a doorway 55 space. A door 56 is coupled through hinge 58 to the hinge cell 52. The door 56 pivots (along arrow A of FIG. 1) between an open orientation shown in FIG. 1 and a closed configuration with the door 56 closing off the doorway 55 and with the door 56 abutting against the latch cell 54. An inner face between the door 56 and the latch cell 54 is angled away from perpendicular to an inner surface of the latch cell 54 to ensure a secure fit when the door is closed, and with a small gap. The door 56 preferably has a thickness approximately half of a thickness of the square cells 56 which make up the front wall 44 in which the doorway 55 indoor assembly 50 are located. Where as different types of hinges could be utilized, the hinges are configured to handle the significant weight of the door 56, as the door 56 is typically formed of cementitious material or can be formed of other heavy materials with radiation absorbing characteristics, such as lead.

With particular reference to FIGS. 2-6, particular details of the cells 42, 44, 46, 48, 52, 54 are described, as provided in the embodiment illustrated herein. The cells generally feature undulating surfaces 60 on lateral sides of the cells which are placed adjacent to other cells. These undulating surfaces 60 are non-planar and complementary in shape, and could have a variety of different actual configurations, with an undulating form being one such complementary shape.

With such an undulating surface 60, this surface is characterized by alternating troughs 62 and crests 64 separated by angled facets therebetween which are non-perpendicular to the troughs and non-perpendicular to the crests. The troughs and crests are preferably oriented planar and parallel with each other and offset by an amplitude of the undulating surface. This amplitude is sufficiently great so that even if the adjacent cells are not placed entirely tightly together, that the troughs and crests of adjacent cells overlap each other somewhat. In this way, no linear pathway out of the vault 10 are provided along which radiation can pass. Most preferably, the troughs, crusts and angled facets are planar in form, but they could be curving, such as to give the undulating surfaces 60 a form similar to that of a sine wave.

The crests of one cell 42, 44, 46, 48 extend into the troughs of the other cell 42, 44, 46, 48 when placed in the wall 40. Such semi-interlocking character allows the adjacent cells 42, 44, 46, 48 to support each other structurally and resist many forms of movement therebetween. Furthermore, radiation escape therebetween is inhibited. In one embodiment, the troughs can be slightly deeper than the crests are high. With such slightly truncated crests, the crests would be slightly larger than the troughs in surface area. This would ensure that the crests 64 bottom out adjacent to the troughs 62, but leave a slight space. Such a slight space ensures that the angled facets come tightly into contact with each other when the cells 42, 44, 46, 48 are placed adjacent to each other. In another embodiment, the crests 64 are precisely sized to match each trough 62 for tight tolerance between adjacent cells 42, 44, 46, 48.

To aid in placement of the various cells, top surfaces 61 of the cells feature hooks 68 extending upwardly therefrom. These hooks 68 typically are formed of rebar and extend down into an interior of each cell. The cells are typically formed of cementitious material and include reinforcing bar within an interior thereof. The hooks 68 are formed of sufficiently high strength rebar or other structure embedded within the material forming the cells, so that an entire weight of each cell can be carried by the hooks. Smaller cells can have a singular hook. Larger cells can have multiple hooks. Typically, an overhead crane is utilized which engages with the hooks and then can suspend the cells and carefully placed the cells precisely were desired. Secure and tight placement of the cells adjacent to each other can thus be achieved. As an alternative to the hooks 68 forming a full loop, the hooks could be anchored only at one end and still curve to allow for engagement with a crane or other lifting apparatus.

After placement of each cell 42, 44, 46, 48, and to keep the cells securely in position, brackets 66 are utilized. Each bracket 66 preferably includes a pair of plates which are perpendicular to each other and with each plate of each bracket having two holes 67 therein. These brackets 66 are placed at a junction between the surface 22 of the foundation 20 and a lower portion of an inner surface of each cell 42, 44, 46, 48. Wider cells can optionally have multiple brackets thereon. Fasteners such as bolts pass through the holes 67 and then into holes formed in the surface 22 of the foundation 20 and into the cells adjacent where the holes 67 in the bracket 66 are located. These bolts can then be anchored, such as utilizing epoxy, so that secure attachment is provided. As an alternative, threaded sleeves could be embedded within the concrete or other material forming the cells, so the threading of the bolts could occur. Similarly, anchor bolts could extend up from the foundation at strategic locations and then nuts would be placed on such bolts after the bolts pass-through holes 67 in the brackets 66. After the bracket 66 have been secured in place with appropriate fasteners, the cells forming the walls 40 are securely anchored to the foundation 20.

Figure 12:
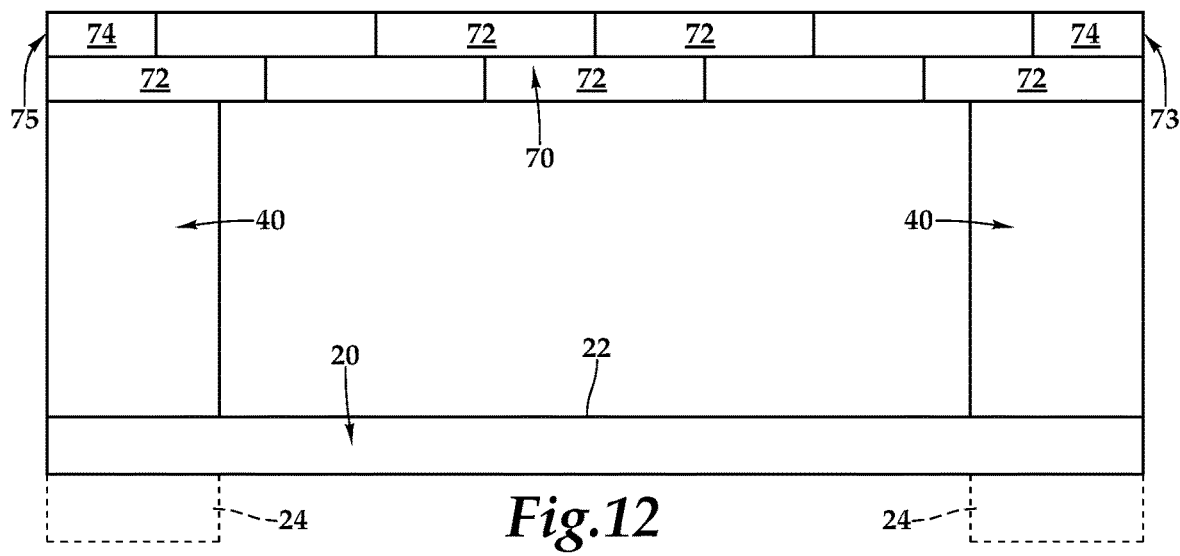
FIG. 12 is a front elevation full sectional view of the oncology vault of this invention and showing the foundation, walls and ceiling assembled together, and with optional footings beneath the foundation shown in broken lines.

With particular reference to FIGS. 7-14, details of the ceiling 70 are described, as disclosed in this particular embodiment. The ceiling 70 is formed of various ceiling slab elements 72, 74 resting upon upper portions of the walls 40, defined by top surfaces 61 of the various cells 42, 44, 46, 48, 52, 54. In the first embodiment, depicted in FIGS. 7-9, 12 and 13, two layers of slabs 72, 74 are provided to form the ceiling 70, including a lower layer 73 and an upper layer 75. The lower layer 73 is formed a full slabs 72. The upper level 75 is also formed of full slabs 72, except at ends of the upper level 75, where two half slabs 74 are placed (FIGS. 9 and 12). The full slabs 72 are twice as wide as the half slabs 74 (FIGS. 10 and 11). Otherwise, the slabs 72, 74 are similar to each other (except as to the number of brackets 66 and hooks 68 include thereon). By utilizing half slabs 74 in the upper layer 75 at the ends of the ceiling 70, seams between adjacent slabs 72, 74 within the layers are offset relative to each other. With such offsetting of the seams, no linear path is provided for radiation to escape the vault 10 through the ceiling 70.

Brackets 66 are provided on lower portions of the slab 72, 74 adjacent to where they overlay top surfaces 61 of various cells of the walls 40. These brackets 66 can thus accommodate fasteners to secure the ceiling 70 in place. In one embodiment, recesses are provided in an undersurface of each slab 72, 74 at strategic locations to allow the hooks 68 on the top surfaces 61 of the cells forming the walls 40 to fit up into these recesses and allow for the slabs 72, 74 to fit flush upon the top surfaces 61 of the cells forming the walls 40. The hooks 68 and such recesses can also aid in securely holding the ceiling 70 relative to the walls 40.

In an alternative ceiling 80 (FIG. 14), a series of interlocking slabs 76 are utilized in a single layer. These interlocking slabs 76 include undulating surfaces 60 on lateral sides thereof which allow these interlocking slabs 76 to lock together and also to eliminate linear pathways along seams therebetween. End interlocking slabs 78 are also provided which are typically wider and only include an undulating surface 60 on one side thereof. As an alternative, a mixture of interlocking slabs 76 and full slabs 72 could be utilized together as a hybrid between the embodiment of FIGS. 12 and 13 and the embodiment of FIG. 14.

Hooks 68 are provided on the slabs 72, 74, 76 forming the ceiling 70 (FIGS. 10, 11 and 15). The hooks 68 are preferably provided at ends of each slab 72, 74, 76, either singularly or in a pair, depending on the size of the slab. These hooks 68 allow for placement of the ceiling slabs precisely where desired while utilizing equipment such as an overhead crane.

In various different embodiments access is provided into the vault for various "services" such as ventilation, water plumbing and electrical wiring. In on embodiment, all such services are provided through the foundation and are formed in advance when pouring the foundation. Undulating pathways can be built into all such service conduits to prevent radiation escape. Similarly, such pathways for services could be provided through the walls or through the ceiling 70 by being formed within the various cells forming the walls 40 or various slabs forming the ceiling 70. Any such conduit pathways through these cells in the walls 40 or slabs in the ceiling 70 would preferably be bending in character so that such service access ports would not provide a straight line path and an opportunity for radiation leakage out of the vault 10.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. An oncology vault, comprising:
   a foundation composed of cementitious material;
   a plurality of movable wall cells resting upon said foundation, each wall cell including an inside surface, an outside surface opposite said inside surface, and two lateral sides having mating surfaces of non-planar complementary undulating shape with adjacent lateral surfaces of adjacent said wall cells, said undulating shape including alternating crests and troughs that are flat and parallel with each other and offset by angled facets non-perpendicular to said troughs and non-perpendicular to said crests; said wall cells surrounding a majority of a perimeter of the vault; and
   a ceiling positioned above said wall cells, said ceiling defined by a plurality of ceiling slab elements resting upon said walls including both a lower layer of ceiling slab elements and an upper layer of ceiling slab elements, with seams between adjacent said ceiling slab elements in said lower layer offset relative to seams between said ceiling slab elements in said upper layer.

2. The vault of claim 1 wherein one or more of said wall cells have different thicknesses between an innermost surface and an outermost surface, so that said wall cells provide different wall thicknesses at different portions of the vault.

3. The vault of claim 1 wherein said angled facets are angled between 15° and 45° away from perpendicular to said crests and said troughs.

4. The vault of claim 1 wherein said foundation includes an equipment pit extending down below a surface of said foundation at a central portion of said foundation.

5. The vault of claim 1 wherein each said wall cell includes at least one grabbable bar on an upper portion thereof, anchored to said wall cell for moving said wall cell.

6. The vault of claim 5 wherein said grabbable bar includes a hook with two ends embedded in said wall cell.

7. The vault of claim 1 wherein said ceiling slab elements are formed of cementitious material.

8. The vault of claim 7 wherein said ceiling slab elements include at least one lateral side having a mating surface of non-planar complemental shape with adjacent lateral surfaces of adjacent said ceiling slab elements.

9. The vault of claim 8 wherein said mating surfaces of said ceiling slab elements have an undulating form including alternating crests and troughs.

10. A method of building a modular oncology vault structure, including the steps of:
    forming a foundation of cementitious material;
    placing a plurality of movable wall cells resting upon the foundation, each wall cell including an inside surface, an outside surface opposite the inside surface, and two lateral sides between the inside surface and the outside surface and opposite each other, the lateral sides having mating surfaces of non-planar complementary undulating shape with adjacent lateral surfaces of adjacent wall cells, said undulating shape including alternating crests and troughs that are flat and parallel with each other and offset by angled facets non-perpendicular to said troughs and non-perpendicular to said crests, the wall cells surrounding a majority of a perimeter of the vault; and
    covering a space inboard of the wall cells with a ceiling by stacking a plurality of ceiling slab elements resting upon said walls to form both a lower layer of ceiling slab elements and an upper layer of ceiling slab elements, with seams between adjacent said ceiling slab elements in said lower layer offset relative to seams between said ceiling slab elements in said upper layer.

11. The method of claim 10 wherein said placing step includes the mating surfaces of the wall cells having an undulating form including alternating crests and troughs.

12. The method of claim 10 wherein said placing step includes each of the wall cells having at least one grabbable bar on a top surface thereof, the grabbable bar anchored to the wall cell for moving the wall cell during said placing step.

13. The method of claim 10 wherein the seams between the ceiling slab elements have a mating surface of non-planar complemental shape with adjacent lateral surfaces of adjacent ceiling slab elements.

14. The method of claim 13 wherein the mating surfaces of the ceiling slab elements have an undulating form including alternating crests and troughs.

\* \* \* \* \*